(12) United States Patent
Momose

(10) Patent No.: US 7,180,979 B2
(45) Date of Patent: Feb. 20, 2007

(54) X-RAY IMAGING SYSTEM AND IMAGING METHOD

(76) Inventor: Atsushi Momose, 2-19-4, Misono, Moriya-shi, Ibaraki (JP)

( * ) Notice: Subject to any disclaimer, the term of this patent is extended or adjusted under 35 U.S.C. 154(b) by 0 days.

(21) Appl. No.: 11/159,568

(22) Filed: Jun. 22, 2005

(65) Prior Publication Data

US 2005/0286680 A1 Dec. 29, 2005

Related U.S. Application Data

(63) Continuation-in-part of application No. PCT/JP03/16670, filed on Dec. 25, 2003.

(30) Foreign Application Priority Data

Dec. 26, 2002 (JP) ............................. 2002-376018

(51) Int. Cl.
*G01N 23/04* (2006.01)
(52) U.S. Cl. ............................. 378/62; 378/87; 378/70
(58) Field of Classification Search .................. 378/62, 378/87, 70, 71, 2, 82, 84–85
See application file for complete search history.

(56) References Cited

U.S. PATENT DOCUMENTS 5,812,629 A * 9/1998 Clauser ...................... 378/62

FOREIGN PATENT DOCUMENTS

JP 10-248833 A 9/1998

* cited by examiner

*Primary Examiner*—Edward J. Glick
*Assistant Examiner*—Hoon Song
(74) *Attorney, Agent, or Firm*—Christensen O'Connor Johnson Kindness PLLC

(57) ABSTRACT

The present invention provides an apparatus capable of X-ray imaging utilizing phase of X-rays. An X-ray imaging apparatus equipped with first and second diffraction gratings and an X-ray image detector are described. The first diffraction grating generates a Talbot effect and a second diffraction grating diffracts X-rays diffracted by the first diffraction grating. An image detector is provided to detect the X-rays diffracted by the second diffraction grating. In this manner, image contrasts caused by changes in phase of X-rays due to a subject arranged in front of the first diffraction grating or between the first diffraction grating and the second diffraction grating can be achieved.

13 Claims, 5 Drawing Sheets

X-RAY IMAGING SYSTEM AND IMAGING METHOD

CROSS-REFERENCE TO RELATED APPLICATION

This application is a continuation-in-part application of International Application No. PCT/JP03/16670, filed Dec. 25, 2003, incorporated herein by reference.

FIELD OF THE INVENTION

The present invention relates to an X-ray imaging apparatus utilizing phase of X-rays.

RELATED ART

In the visible light region, a Talbot interferometer where a Talbot effect is generated by a diffraction grating and a moiré fringe is generated by combining another diffraction grating is well-known. As a result, it is possible to visualize wavefronts of visible light, i.e. to generate image contrast utilizing phase.

In the X-ray region, research and development of X-ray imaging apparatus employing phase, as disclosed, for example, in Japanese Patent Laid-open Publication H10-248833, is also well-known. However, there are drawbacks with this technology in that the apparatus configuration is complex or a large-scale X-ray source such as a synchrotron radiation source is necessary.

SUMMARY OF THE INVENTION

The present invention therefore sets out to resolve this situation. The object of the present invention is to provide an apparatus capable of X-ray imaging utilizing phase of X-rays with a simple construction.

The X-ray imaging apparatus of the present invention is equipped with first and second diffraction gratings and an X-ray image detector. The first diffraction grating is constructed to generate a Talbot effect in X-rays diffracted by the first diffraction grating. The second diffraction grating is configured so as to diffract the X-rays diffracted by the first diffraction grating. The X-ray image detector is configured so as to detect the X-rays diffracted by the second diffraction grating.

By diffracting X-rays diffracted by the first diffraction grating, the second diffraction grating is capable of forming image contrast caused by changes in phase of X-rays due to the subject arranged in front of the first diffraction grating or between the first diffraction grating and the second diffraction grating. The X-ray image detector is capable of detecting X-rays creating image contrast.

By diffracting X-rays diffracted by the first diffraction grating, the second diffraction grating is capable of forming image contrast caused by changes in phase of X-rays due to the subject arranged in front of the front surface of the first diffraction grating or between the first diffraction grating and the second diffraction grating. The X-ray image detector is capable of detecting X-rays creating image contrast.

The first and second diffraction gratings may be taken to be transmission-type gratings.

The X-ray imaging apparatus may also be provided with an X-ray source. This X-ray source emits X-rays on the X-ray image detector via the first diffraction grating and the second diffraction grating.

The ratio between the distance from the X-ray source to the first diffraction grating and the period at the first diffraction grating, and the ratio of the distance from the X-ray source to the second diffraction grating and the period at the second diffraction grating may be set to be substantially the same.

The first diffraction grating may also generate a phase modulation of approximately 55 degrees to 125 degrees or preferably 80 degrees to 100 degrees to X-rays with which the first diffraction grating is irradiated.

The periods of the first and second diffraction gratings may be set to be substantially equal.

Moiré fringes may also be formed at an X-ray image detected by the X-ray image detector.

The first and second diffraction gratings may be taken to be rotatable in a relative manner, and the spacings of the moiré fringes may also be adjustable.

The first and second diffraction gratings may comprise diffraction members for diffracting the X-rays. The diffraction members may extend in at least one direction. The first diffraction grating or the second diffraction grating may then be capable of moving along these diffraction grating surfaces and along the direction of intersection at the diffraction member.

The tomography apparatus of the present invention acquires phase shift differential images from X-ray images acquired by the X-ray imaging apparatus, acquires phase shift images from the phase shift differential images, and acquires a solid image from the phase shift images.

The second diffraction grating of the X-ray imaging apparatus of the present invention may form moiré fringes by diffracting the X-rays diffracted by the first diffraction grating. The X-ray image detector may be constructed to detect X-rays forming the moiré fringes.

The X-ray imaging method of the present invention employs an X-ray source, first and second diffraction gratings, and an X-ray image detector, and comprises the following steps.

(1) a step of arranging a test subject between the X-ray source and the first diffraction grating or between the first diffraction grating and the second diffraction grating;

(2) a step of irradiating the first diffraction grating with X-rays from the X-ray source;

(3) a step of irradiating the second diffraction grating with the X-rays, which are diffracted by the first diffraction grating so as to exhibit the Talbot effect;

(4) a step of diffracting the X-rays diffracted by the first diffraction grating using the second diffraction grating; and (5) a step of the X-ray image detector detecting the X-rays diffracted by the second diffraction grating.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The following is a description of an X-ray imaging apparatus of a first embodiment of the present invention. The imaging apparatus is mainly constituted by an X-ray source 1, a first diffraction grating 2, a second diffraction grating 3, and an X-ray image detector 4 (refer to FIG. 1). The X-ray source 1 is taken to have "spatial coherency high enough to cause the Talbot effect when the first diffraction grating 2 is irradiated with the X-rays from the X-ray source 1." For example, "assuming an X-ray source size (i.e. X-ray source opening diameter) of the order of 30 microns, spatial coherency at a position of approximately five meters or more from the X-ray source" corresponds to this.

The Talbot effect is the phenomenon that "when light having spatial coherency of the extent described above is transmitted or reflected by an object having a certain periodic structure, a phenomena where a spatial distribution (hereinafter referred to as a "self image") of light of a period corresponding to the period of the object occurs at positions distanced from the object by certain specific distances decided by the central wavelength of the light and the period of the object." A similar phenomena also occurs in the vicinities of the specific distances described above. In this specification, the Talbot effect is the phenomena where a self image appears at the specific distances or in the vicinities thereof.

The conditions under which a Talbot interferometer is constituted by the X-ray source 1, diffraction grating 2 and diffraction grating 3 are as-fellows described later.

Figure 2:
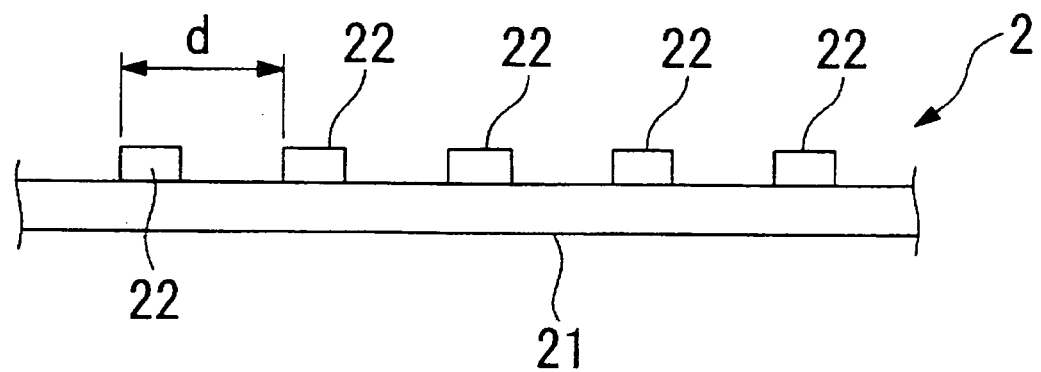
FIG. 2 is a cross-sectional view of a first diffraction grating.
Figure 3:
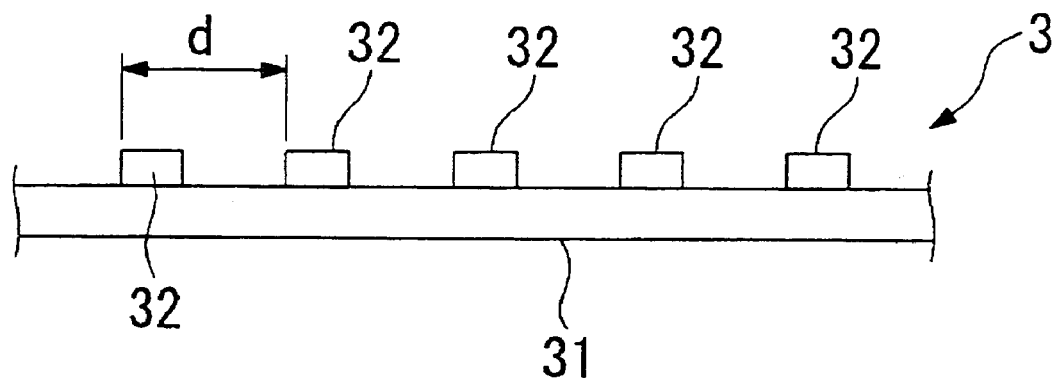
FIG. 3 is a cross-sectional view of a second diffraction grating.

The first diffraction grating 2 is equipped with a substrate 21 and a plurality of diffraction members 22 fitted to the substrate 21 (refer to FIG. 2). The substrate 21 is, for example, glass. The plurality of diffraction members 22 are line shaped and each extend in one direction (in the normal direction of the paper surface in FIG. 2). In this embodiment, pitch (i.e. the periods of the diffraction gratings) d of the plurality of diffraction members 22 is constant (i.e. there are equal gaps between the diffraction members 22). For example, gold may be used as a material for the plurality of diffraction members 22. It is preferable for the diffraction grating 22 to be a so-called phase-type diffraction grating giving a phase modulation of approximately 55 to 125 degrees or preferably approximately 80 to 100 degrees (ideally 90 degrees) X-rays. Namely, the diffraction member 22 changes the phase velocity of X-rays impinging on this portion. It is by no means necessary for the X-rays to always be monochromatic, and may have an energy width (i.e. wavelength spectral width) of a range satisfying the aforementioned conditions.

As with the first diffraction grating 2, the second diffraction grating 3 is equipped with a substrate 31 and diffraction members 32. The second diffraction grating 3 is constructed to form image contrast by diffracting X-rays diffracted by the first diffraction grating 2. The second diffraction grating 3 is preferably an amplitude-type diffraction grating employing thicker diffraction members 32.

An X-ray image detector 4 detects X-rays generating image contrast. This detector 4 is the same as that used in an X-ray imaging apparatus of the related art and is therefore not described in detail here.

Next, a description is given of conditions for constructing-a Talbot interferometer with the first and second diffraction gratings 2 and 3. First, the coherence length is as follows.

$$l = \frac{\lambda}{a/(L + Z_1 + Z_2)} \quad \text{(equation 1)}$$

Figure 4:
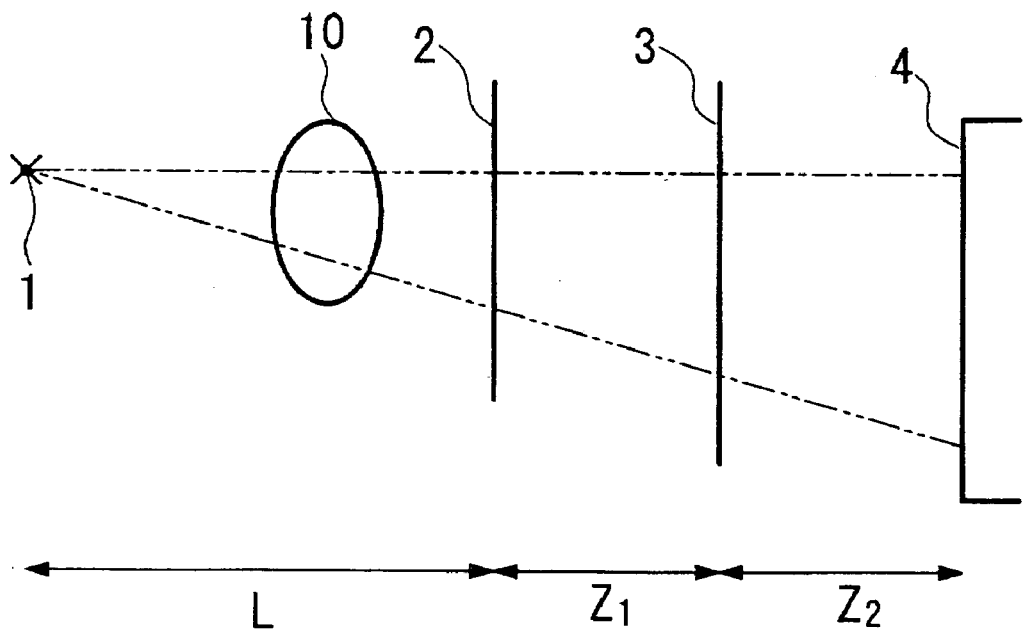
FIG. 4 is a side view of the X-ray imaging apparatus of FIG. 1.

Here, $\lambda$: wavelength of X-rays (normally, central wavelength)

a: diameter of opening of X-ray source in the direction substantially orthogonal to the diffraction member, L: distance from X-ray source to first diffraction grating (refer to FIG. 4)

Z1: distance from first diffraction grating to second diffraction grating,

Z2: distance from second diffraction grating to detector.

Further, the distance Z1 between the first diffraction grating 2 and the second diffraction grating 3 has to substantially satisfy the following conditions assuming that the first diffraction grating 2 is a phase-type diffraction grating:

$$Z_1 = \left(m + \frac{1}{2}\right)\frac{d^2}{\lambda} \quad \text{(equation 2)}$$

where m is an integer, and d is the period of the aforementioned diffraction grating. Here, when l=αd, it is preferable for α in equation (1) to be α>5(m+½).

Next, a description is given of the operation of an X-ray imaging apparatus of the present invention.

This imaging apparatus is used with a test subject 10 (refer to FIG. 1 and FIG. 4) arranged between the X-ray source 1 and the first diffraction grating 2. Next, X-rays are emitted from the X-ray source 1 to the first diffraction grating 2. The X-rays pass through the first diffraction grating 2, and the Talbot effect is generated by the first diffraction grating 2. Namely, when plane waves pass through the diffraction grating, in the case of a phase-type diffraction grating, self-images of the diffraction grating are formed at distances close to the values provided in equation (2). In the current case, there is distortion in the wave front of the X-rays incident to the first diffraction grating 2 because of the shift in the phase of the X-rays due to the test subject 10. The self image of the first diffraction grating 2 is dependent on the distortion and is therefore deformed. Next, the X-rays pass through the second diffraction grating 3. As a result, it is possible to generate image contrast for the X-rays by overlapping the self image of the first diffraction grating 2 deformed as described above and the second diffraction grating 3. The image contrast is typically moiré fringes that can be detected by the X-ray image detector 4. The generated moiré fringes are modulated by the test subject 10. The modulation amount depends (this may be proportionally) on the angle of X-ray deflection as a result of refraction effects at the test subject 10. It is possible to detect the test subject 10 and the internal structure by analyzing the moiré fringes detected by the X-ray image detector 4.

The diffraction members of the first and second diffraction gratings 2 and 3 are taken to be arranged so as to be rotated by just a minute angle θ relatively about a virtual axis passing through the X-ray source and the X-ray image detector. The spacing of the generated moiré fringes then changes depending on θ. In the absence of the test subject 10, the spacing of the moiré fringes is given by d/θ. Here, d is the period of the diffraction grating. If a mechanism (for example, a mechanism such as rotating one of the first diffraction grating 2 and the second diffraction grating 3 relatively with respect to the other) for changing the minute angle θ is provided, it is possible to adjust the moiré fringes so as to be preferable for observation. Further, if the minute angle θ is adjusted to by substantially zero, moiré fringes do not appear outside portions corresponding to the test subject 10 (i.e. at non-modulated portions). As a result, only contrast appears due to the test subject 10 in the obtained X-ray image.

Further, in the example described above, a description is given of the case of positioning the test subject 10 between the X-ray source 1 and the diffraction grating 2. However, it is also possible for the self image of the diffraction grating 2 generated at the position of the diffraction grating 3 to be transformed by the test subject 10 even in cases where the test subject 10 is positioned between the diffraction grating 2 and diffraction grating 3. In this case also, it is possible to detect moiré fringes (image contrast) resulting from modulation caused by the test subject 10 in a substantially similar manner to the example described above using the X-ray image detector. Namely, the apparatus of this embodiment is also effective in imaging in the case of positioning the test subject 10 between the diffraction grating 2 and the diffraction grating 3.

According to the apparatus of this embodiment, there is the advantage that it is possible to implement X-ray imaging using a straightforward configuration for subjects that are difficult to observe using conventional methods where contrast generation relies on the magnitude of absorption of X-rays.

EXPERIMENTAL EXAMPLE 1

Experimental example 1 shows the occurrence of the Talbot effect due to irradiation of a diffraction grating with X-rays.

Experimental Conditions

X-rays used: light of wavelength 0.1 nm emitted by a synchrotron.

Diffraction grating: Gold pattern approximately 1 micron thick formed with a period d=8 microns on a 150 micron-thick glass plate.

The conditions for generating the Talbot effect using phase-type diffraction gratings are:

$$Z = \left(m + \frac{1}{2}\right)\frac{d^2}{\lambda}$$

Figure 5:
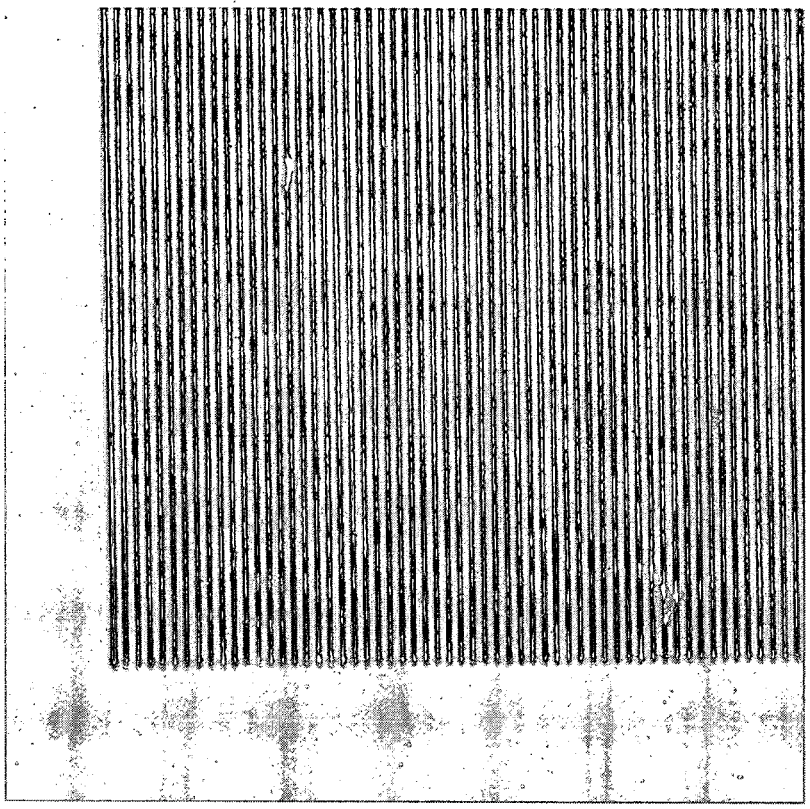
FIG. 5 is a view showing experimental results for the X-ray Talbot effect of experimental example 1, and is a view showing when a distance from a diffraction grating to a measurement surface is 32 cm.
Figure 6:
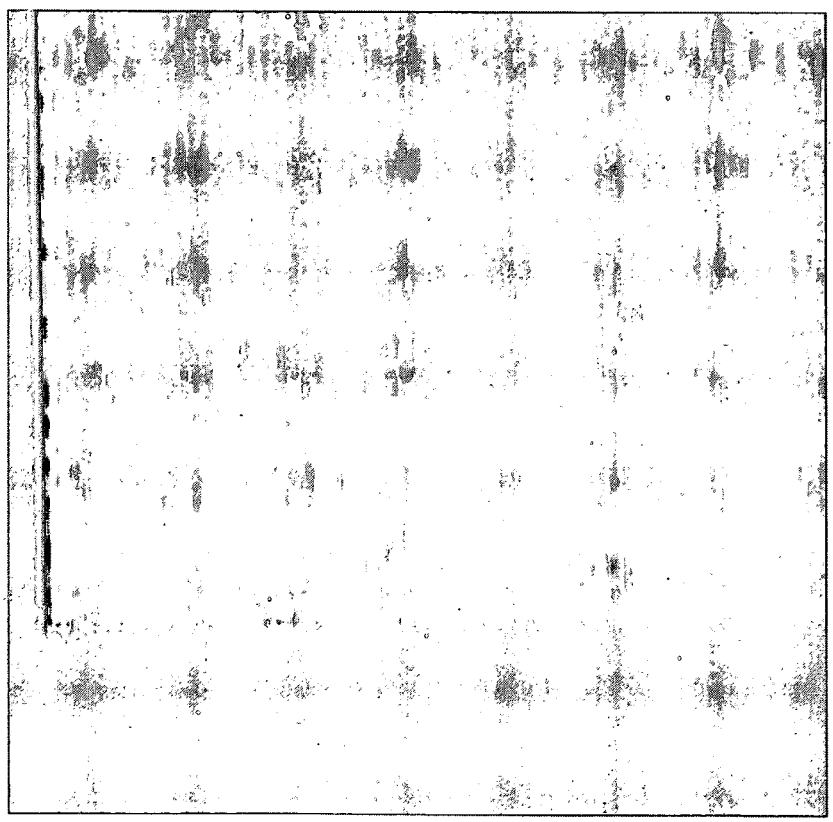
FIG. 6 is a view showing experimental results for the X-ray Talbot effect of experimental example 1, and is a view showing when a distance from a diffraction grating to a measurement surface is 64 cm.
Figure 7:
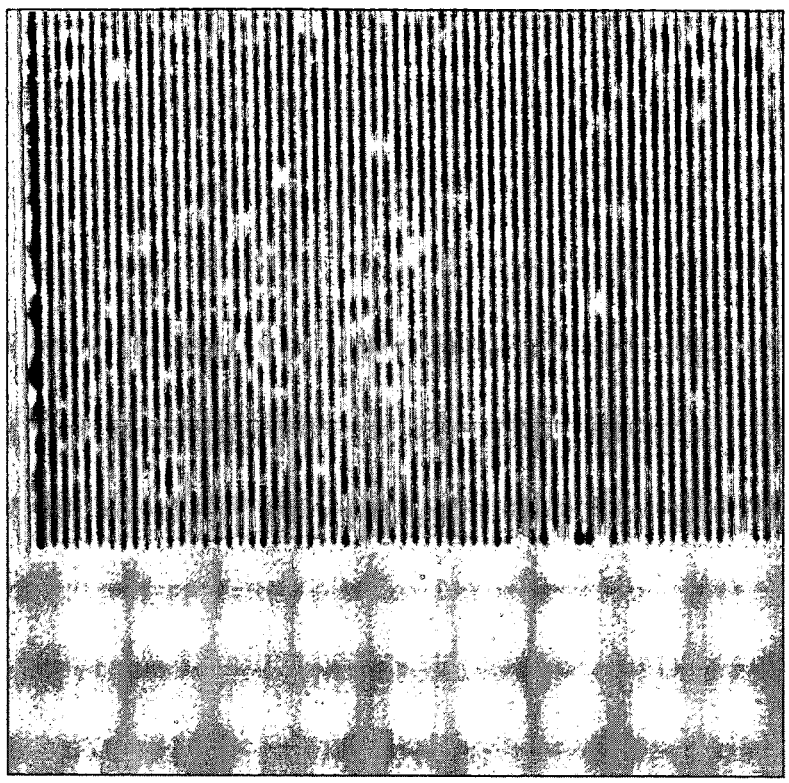
FIG. 7 is a view showing experimental results for the X-ray Talbot effect of experimental example 1, and is a view showing when a distance from a diffraction grating to a measurement surface is 96 cm.

Therefore, first, corresponding with when m=0, a self image of the diffraction grating should be formed when the distance Z from the first diffraction grating 2 to the detection surface is 32 cm. An X-ray image detector is then positioned at a position where the distance Z is 32 cm, and an image is recorded. The results is shown in FIG. 5. Similarly, when the distance Z is 64 cm, this situation is the most away from the above condition, and the self image is therefore unclear (FIG. 6). When the distance Z is 96 cm, a self-image of the diffraction grating can again be formed corresponding to the case where m=1 (FIG. 7). As a result, generation of the Talbot effect is exhibited.

In experimental example 1, a high-resolution X-ray image detector is used with the objective of directly monitoring a self-image but in the case of use with a Talbot interferometer it is necessary only to monitor the moiré fringes and a high-resolution X-ray image detector is therefore not essential.

EXPERIMENTAL EXAMPLE 2

An experimental example 2 of the embodiment utilizing the X-ray Talbot effect is shown here.

Experimental Conditions

X-rays used: light of wavelength 0.1 nm emitted by a synchrotron.

Diffraction grating 2: Gold pattern approximately 1 micron thick formed with a period d=8 microns on a 150 micron-thick glass plate.

Diffraction grating 3: Gold pattern approximately 8 micron thick formed with a period d=8 microns on a 150 micron-thick glass plate.

Spacing Z1 of the diffraction gratings 2 and 3 is taken to be 32 cm for the Talbot effect to appear due to the diffraction grating 2. A plastic sphere approximately 1 mm in diameter is used as the test subject 10.

The test subject 10 is positioned between the X-ray source 1 and the first diffraction grating 2 just in front of the first diffraction grating 2.

Figure 8:
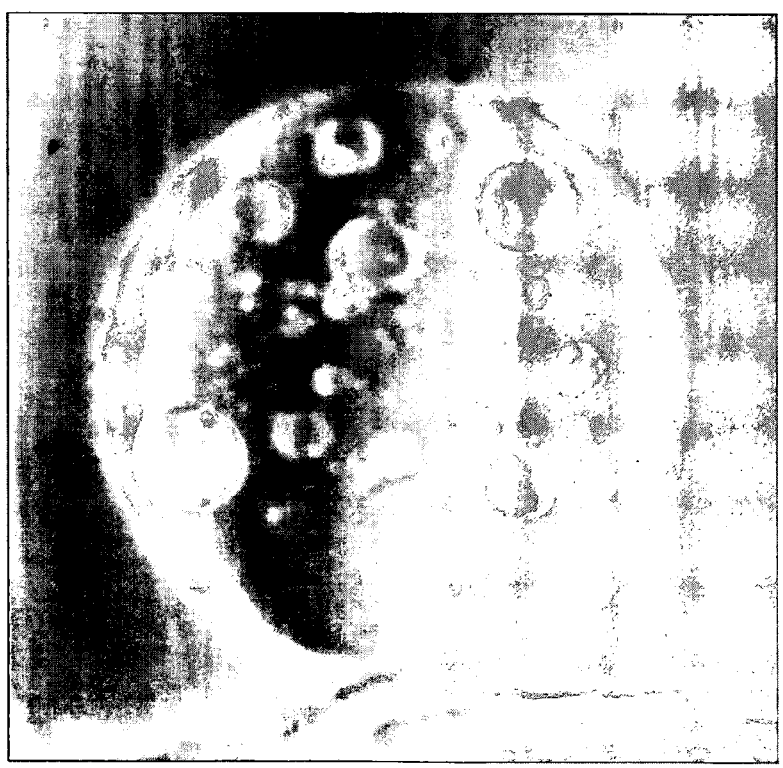
FIG. 8 is a view showing an experimental result for an X-ray Talbot interferometer of an experimental example 2.

X-rays emitted from the X-ray source are detected by the X-ray image detector arranged just behind the diffraction grating 3. As a result, it is possible to obtain the image shown in FIG. 8. In this experimental example, adjustment takes place so that θ≈0°. Moiré fringes therefore substantially do not appear and only contrast corresponding to shifts in phase due to a plastic sphere taken as a subject appears. In this practical example, the sphere and bubbles existing within the sphere are clearly caught.

In experimental example 2, the first and second diffraction gratings are taken to be transmission gratings but may also be reflective gratings. However, the reflectivity of X-rays is typically small, and efficiency is better with transmission-type gratings.

Figure 1:
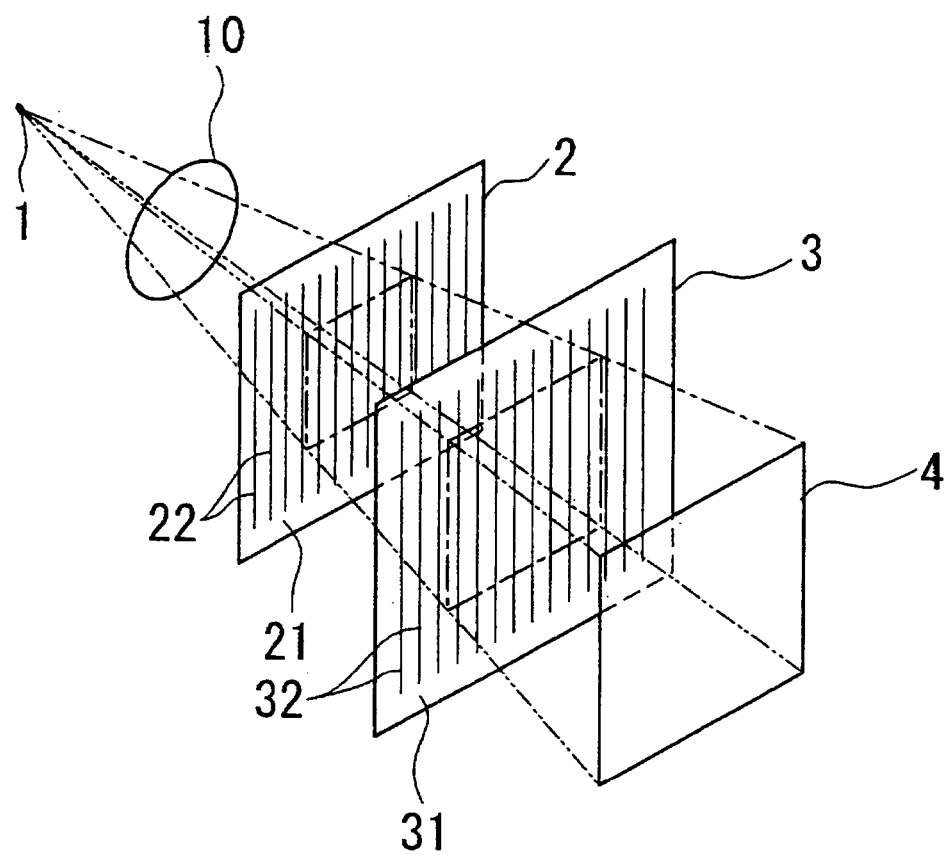
FIG. 1 is a view illustrating an outline configuration for an X-ray imaging apparatus of an embodiment of the present invention.

Further, in experimental example 2, the periods of the first and second diffraction gratings 2 and 3 are taken to be similar or the same but this is because the assumption that the distance L to the X-ray source is sufficiently large compared to the distance Z1 shown in FIG. 1 is possible. Typically, it is preferable for the ratio between the distance from the X-ray source 1 to the first diffraction grating 2 and the period at the first diffraction grating, and the ratio of the distance from the X-ray source 1 to the second diffraction grating and the period at the second diffraction grating 3 to be substantially the same.

Further, in experimental example 2, the first diffraction grating is of a configuration (phase-type diffraction grating) for providing a phase modulation to X-rays but a configuration (amplitude type diffraction grating) providing an intensity modulation to the X-rays is also possible. In this event, the diffraction member may be configured to absorb X-rays. It is possible to configure a Talbot interferometer using the aforementioned principle as well.

Further, in the aforementioned experimental example 2, the first and second diffraction gratings are flat but may also have a spherical surface. In this event, the X-ray source is located preferably at the position of the center of curvature of the spherical surface.

In the aforementioned embodiments, one of either the subject or the imaging system (X-ray source, each diffraction grating, and detector) is rotated and images are acquired using a plurality of photographing directions. These images are then processed by tomography so that the subject and its inner structures can be observed in three dimensions. In this event, a three-dimensional image maps the refractive index distribution, which is different from conventional tomography, and it is therefore possible to reveal the structures that were difficult to extract with the sensitivity of tomography of the related art.

EXPERIMENTAL EXAMPLE 3

Here, an experimental example of tomography is shown using the apparatus of this embodiment.

Experimental Conditions

The experimental conditions of experimental example 3 are the same as for experimental example 2.

The tomography employing this embodiment requires the following three procedures. Procedure 1 transforms X-ray images (hereinafter referred to as "moiré fringe images") detected by the X-ray image detector 4 to "a distributed image of the X-ray deflection angle caused by refraction effects at the test subject 10" (hereafter referred to as a "phase shift differential image"). Procedure 2 acquires an image (hereinafter referred to as a "phase shift image") mapping the shifts in phase by integrating the phase shift differential image. Procedure 3 reconstructs a three-dimensional image using tomography from phase shift images acquired in a plurality of photographing directions.

Procedure 1 employs a fringe scanning technique; that is one of diffraction grating 2 or diffraction grating 3 is displaced relatively against the other. The displacement direction is substantially parallel to the surface of the diffraction grating and along to the direction of intersection at the diffraction members. In the event that tomography is carried out by the apparatus of this embodiment, it is therefore, preferable to provide a mechanism for the displacement of the first diffraction grating or the second diffraction grating 3 at the apparatus of this embodiment.

The moiré fringes move in accompaniment with the displacement of the diffraction grating, and the moiré fringe image returns to the original when the translation distance reaches one period of the diffraction grating. The fringe scanning method performs the displacement by on integer portion of one period at a time and records changes in the moiré fringe image, and calculates a phase shift differential image ϕ (x, y) from the moiré fringe images. (x, y) are coordinates indicating the positions of pixels. The amount of the displacement is taken to be ξ, and a moiré fringe image I (x, y) is typically given by:

$$I(x, y) = A_0 + \sum_{k>0} A_k \cos\left[\frac{2\pi k}{d}\{\Delta(x, y) + Z_1 \varphi(x, y) + \xi\}\right]$$

(equation 3) Here, Ak (k=0, 1, . . . ) is a constant determined by the shape of the diffraction gratings and the properties of the X-ray source. Δ (x, y) describes the contrast generated due to the distortion, manufacturing errors, and arrangement errors of the diffraction gratings, regardless of the subject. d is the period of the diffraction grating subjected to the displacement, and Z1 is the spacing between diffraction grating 2 and diffraction grating 3. Now, while ξ is changed by a step of d/M (M: integer), M moiré fringe images are obtained. If the term for k>N is assumed to be sufficiently small and negligible in equation (3), for M selected so that M>N+1, $$\frac{2\pi}{d}\{\Delta(x, y) + Z_1\varphi(x, y)\} = \arg\left[\sum_{p=1}^{M} I_p(x, y) \exp\left(-2\pi i \frac{p}{M}\right)\right]$$

is satisfied, where arg[ ] refers to extraction of argument. Ip(x,y) are the values of equation (3) when ξ=pd/M. d and Z1 are already known, and Δ (x, y) may be obtained in advance by carrying out a similar measurement when there is no object (i.e. ϕ (x, y)=0). It is therefore possible for ϕ. (x, y) to be obtained from the above.

Figure 9:
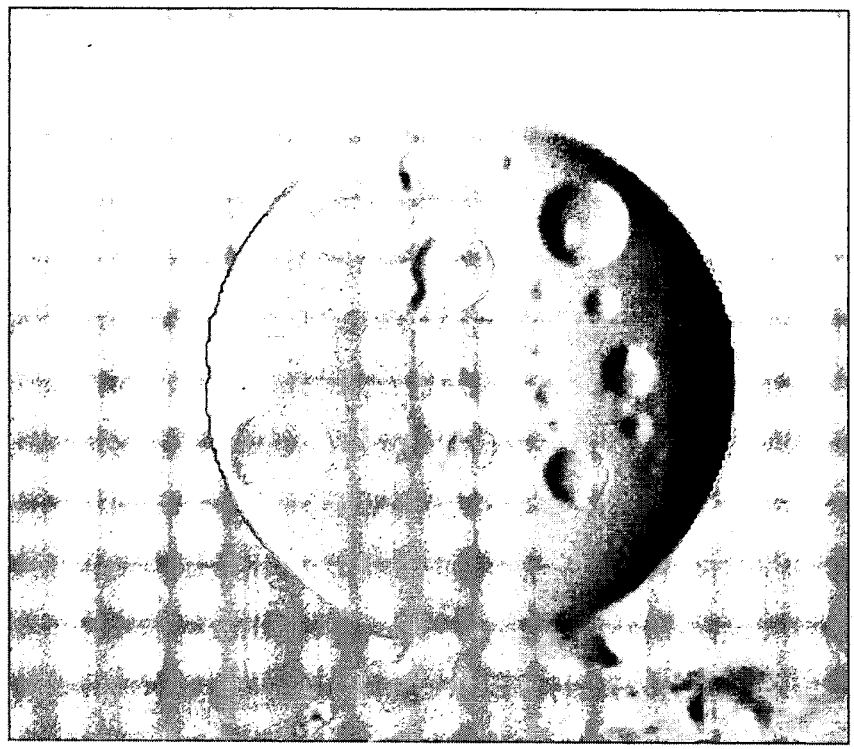
FIG. 9 is a view showing a phase shift differential image obtained in an experimental example 3.

A phase shift differential image ϕ (x, y) obtained from images acquired by the displacement of the second diffraction grating 3 using M=5 is shown in FIG. 9. A plastic sphere approximately 1 mm in diameter is used as the test subject 10 (as in the example of FIG. 8). In FIG. 9, a phase shift differential image is depicted including bubbles contained in the plastic sphere.

The phase shift image Φ (x, y) and the phase shift differential image ϕ(x, y) are correlated using:

$$\varphi(x, y) = \frac{\lambda}{2\pi} \frac{\partial \Phi(x, y)}{\partial x}$$

Here, x corresponds with the displacement direction of the diffraction grating by the fringe scanning techniques. As a result, the phase shift image Φ (x, y) can be provided by integration of the ϕ (x, y) along the X-axis. This is in procedure 2.

The phase shift image Φ (x, y) may be given by taking the refractive index distribution of the subject to be n(x, y, z):

$$\Phi(x, y) = \frac{2\pi}{\lambda} \int [1 - n(x, y, z)]dz$$

Figure 10:
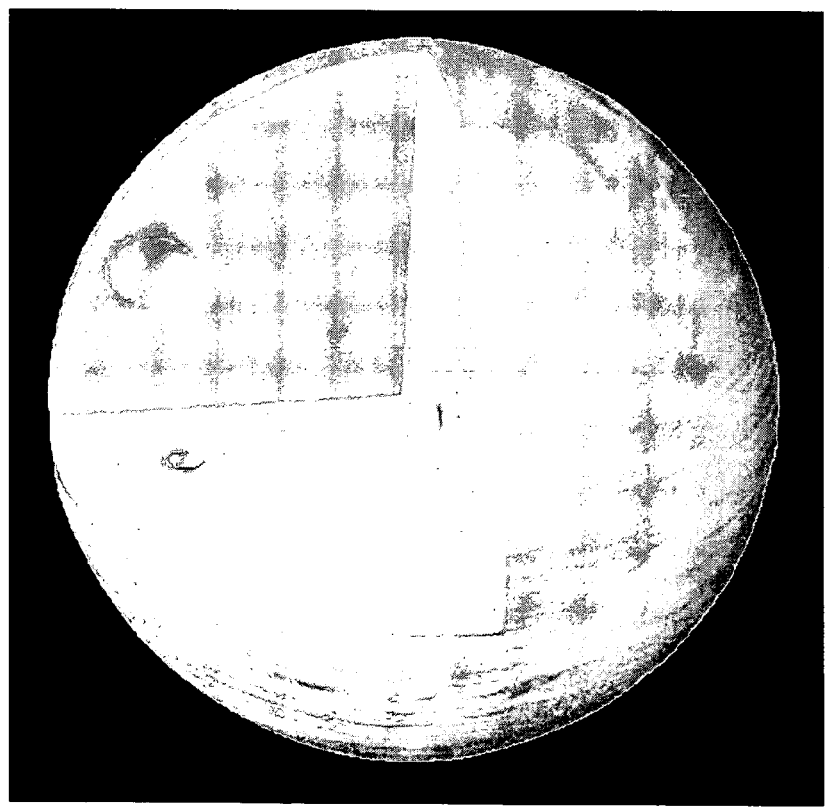
FIG. 10 is a solid image obtained using tomography in experimental example 3.

Here, the z-axis is in the direction of propagation of the X-rays. In the event that a photographed images, which are two-dimensional images, can be acquired from a plurality of photographing direction, topography directions, tomography is technology for re-constructing a three-dimensional image of the subject from these images. Because the phase shift image ϕ (x, y) corresponds to a projection image of 1-n (x, y, z), if phase shift distribution images are obtained from a plurality of photographing directions, it is possible to reconstruct a three-dimensional image indicating n(x, y, z) (Procedure 3). Procedure 2 and Procedure 3 may be carried out collectively at the same time. The results of reconstructing a three-dimensional image using the aforementioned procedures for the plastic sphere of FIG. 9 is shown in FIG. 10. FIG. 10 shows the result reconstructed from 250 of the images such as FIG. 9 acquired by rotating the plastic sphere 0.72 degrees at a time. A portion of the plastic sphere is cropped using computer processing in order to show the inside of the plastic sphere.

This imaging method is by no means meaningless even if advancing as far as procedure 3 does not take place, and sufficient utilization according to the purpose of the imaging is possible for either of an image (raw image) directly obtained by the X-ray image detector 4 of the aforementioned embodiment, a phase shift differential image φ (x, y), or a phase shift image Φ(x, y).

Further, in the aforementioned embodiment, a structure is shown where diffraction members are fitted to a substrate taken as the first and second diffraction gratings, but is by no means limited to this structure. For example, diffraction members may be fitted to both sides of a flat plate to give a diffraction grating structure, with this then being taken as constructing the first and second diffraction members. Further, it is also possible to construct diffraction gratings by alternately overlaying a large number of layers of two types of films or foils with different refractive indexes (or absorbances) and then cutting the stack of films or foils in the thickness direction.

Further, in the aforementioned embodiment, a structure including the X-ray source 1 is adopted but an apparatus that does not have the X-ray source 1 may also be adopted. In this case, at the time of use, the apparatus may then be combined with an X-ray source.

The above described embodiments and practical examples are merely given as examples and in no way show indispensable configurations of the present invention. Various structures are possible without departing from the gist of the present invention.

For example, structural elements occurring in each of the embodiments described above may also exist as function elements, may be united with other elements of the apparatus or parts, or may be implemented as single elements by a plurality of parts.

According to the present invention, it is possible to provide an apparatus capable of X-ray imaging utilizing phase of X-rays using a simple construction.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An X-ray imaging apparatus comprising:
   first and second diffraction gratings; and
   an X-ray image detector,
   wherein the first diffraction grating generates a Talbot effect in the X-rays diffracted by the first diffraction grating, the second diffraction grating diffracts the X-rays diffracted by the first diffraction grating, and the X-ray image detector detects X-rays diffracted by the second diffraction grating,
   wherein the first and second diffraction gratings comprise diffraction members for diffracting the X-rays, the diffraction members extend in at least one direction, and the first diffraction grating or the second diffraction grating are movable along a diffraction grating surface of the first diffraction grating or the second diffraction grating respectively and along a direction of intersection at the diffraction members of the first diffraction grating or the second diffraction grating respectively,
   and wherein the X-ray imaging apparatus further comprises a means for acquiring phase shift differential images using X-ray images acquired by the X-ray image detector, the X-ray images being recorded at appropriate relative displacement of the first diffraction grating against the second diffraction grating induced by the movement of the first diffraction grating or the second diffraction grating.

2. The X-ray imaging apparatus disclosed in claim 1, wherein the first and second diffraction gratings are transmission type diffraction gratings.

3. The X-ray imaging apparatus as disclosed in claim 1, further comprising an X-ray source, wherein the X-ray source irradiating X-rays onto the X-ray image detector via the first diffraction grating and the second diffraction grating.

4. The X-ray imaging apparatus as disclosed in claim 3, wherein a subject is arranged between the X-ray source and the first diffraction grating.

5. The X-ray imaging apparatus as disclosed in claim 3, wherein a ratio of a distance from the X-ray source to the first diffraction grating and the period of the first diffraction grating, and a ratio of a distance from the X-ray source to the second diffraction grating and the period of the second diffraction grating are substantially the same.

6. The X-ray imaging apparatus as disclosed in claim 1, wherein the first diffraction grating is configured so as to provide phase modulation of approximately 55 degrees to 125 degrees with respect to irradiated X-rays.

7. The X-ray imaging apparatus as disclosed in claim 1, wherein periods of the first and second diffraction gratings are substantially equal.

8. The X-ray imaging apparatus as disclosed in claim 1, wherein Moire fringes are formed at an X-ray image detected by the X-ray image detector.

9. The X-ray imaging apparatus as disclosed in claim 8, wherein the first and second diffraction gratings are rotatable relative to each other, and as a result, it is possible for intervals between the Moire fringes to be adjusted.

10. The X-ray imaging apparatus as disclosed in claim 1, wherein spacing between the first diffraction grating and the second diffraction grating allows a subject to be placed between the first diffraction grating and the second diffraction grating.

11. A tomography apparatus, acquiring phase shift images from the phase shift differential images disclosed in claim 1, and acquiring a solid image from the phase shift images.

12. The X-ray imaging apparatus as disclosed in claim 1, wherein the second diffraction grating is configured to form Moire fringes by diffracting the X-rays diffracted by the first diffraction grating, and the X-ray image detector is constructed to detect X-rays forming the Moire fringes.

13. An X-ray imaging method using an X-ray source, first and second diffraction gratings, and an X-ray image detector, comprising the steps of:
   (1) arranging a test subject between the X-ray source and the first diffraction grating or between the first diffraction grating and the second diffraction grating, which are capable of moving along a diffraction grating surface of the first diffraction grating or the second diffraction grating respectively and along a direction of intersection at the diffraction members of the first diffraction grating or the second diffraction grating respectively, wherein the first and second diffraction gratings comprise the diffraction members for diffracting the X-rays, and the diffraction members extend in at least one direction;

(2) irradiating the first diffraction grating with X-rays from the X-ray source;
(3) irradiating the second diffraction grating with the X-rays, which is diffracted by the first diffraction grating so as to bear the Talbot effect;
(4) diffracting the X-rays diffracted by the first diffraction grating using the second diffraction grating;
(5) the X-ray image detector detecting the X-rays diffracted by the second diffraction grating; and
(6) acquiring phase shift differential images using X-ray images acquired by the X-ray image detector, wherein the X-ray images are recorded at appropriate relative displacement of the first diffraction grating against the second diffraction grating induced by the movement of the first diffraction grating or the second diffraction grating.

* * * * *